United States Patent [19]

Prettyjohns

[11] Patent Number: 5,774,214
[45] Date of Patent: Jun. 30, 1998

[54] MULTI-MODE IMAGING APPARATUS FOR RADIATION-EMITTING OR ABSORBING SAMPLES

[75] Inventor: Keith Neil Prettyjohns, Tucson, Ariz.

[73] Assignee: Photometrics, Ltd., Tucson, Ariz.

[21] Appl. No.: 764,305

[22] Filed: Dec. 12, 1996

[51] Int. Cl.$^6$ .................................................. G01N 21/64
[52] U.S. Cl. ......................... 356/344; 356/244; 204/612; 250/458.1
[58] Field of Search ................................. 356/344, 244, 356/246, 440; 204/612, 182.8; 250/458.1, 461.2; 422/102, 82.08, 131

[56] References Cited

U.S. PATENT DOCUMENTS

| | | | |
|---|---|---|---|
| 4,572,671 | 2/1986 | Kaneko | 356/244 |
| 4,682,891 | 7/1987 | de Macario et al. | 356/244 |
| 5,162,654 | 11/1992 | Kostichka et al. | 356/344 |
| 5,307,148 | 4/1994 | Kambara et al. | 356/344 |
| 5,552,322 | 9/1996 | Nemoto et al. | 356/344 |

FOREIGN PATENT DOCUMENTS

| | | | |
|---|---|---|---|
| 0269935 | 11/1990 | Japan | 356/344 |
| 0020644 | 1/1991 | Japan | 356/344 |

*Primary Examiner*—Hoa Q. Pham
*Attorney, Agent, or Firm*—Herbert M. Shapiro

[57] ABSTRACT

A multi-mode apparatus for capturing light patterns emitted or absorbed by a planar sample, such as an electropheresis gel, is made possible by a unique tray and sample holder system which positions a sample at a pre-determined focal plane of the solid state camera integral to the apparatus. Each sample is fixed in a sample holder specific to the mode of labeling of the sample. The tray is configured to retain each sample holder at a different elevation with respect to the side walls of the tray for proper placement of the sample at the focal plane. The tray side walls are adapted to position a sample holder at the proper elevation depending on the sampling mode and illumination technique selected. The sample holder includes a combination of transparent, translucent, or opaque plates designed to allow illumination and imaging of the sample for the particular labeling method employed.

19 Claims, 4 Drawing Sheets

MULTI-MODE IMAGING APPARATUS FOR RADIATION-EMITTING OR ABSORBING SAMPLES

FIELD OF THE INVENTION

This invention relates to apparatus for capturing images from samples such as electrophoresis gels and blots, and, more particularly, to apparatus for sample handling, illuminating and image capturing of radiation patterns emitted or absorbed by such radiation sources.

BACKGROUND OF THE INVENTION

The capture of images from samples such as electropheresis gels, blots and films depends, to a large extent, on the labeling and image capture method employed to produce those images. As is well known in the art, fluorescent, radioisotope, chemiluminescence and densitometer techniques are used. These techniques require different light sources, different sample processes, different sensitivities, some using phosphor screens . . . etc. Consequently, different apparatus has to be used for each technological approach. Further, slow scan cameras have been used in the prior art to capture an image from flourescent and chemiluminescent labeled samples. But, if a slow scan camera is used to capture an image it is difficult to align and pre-focus the sample because the camera operates at a frame rate of only one or two frames per second. Consequently, not only is different apparatus required, but also focusing is a significant problem if a slow scan camera is used. Slow scan cameras have not been used for radioisotope-labeled samples and there has been no attempt to produce a single instrument to implement all the different imaging techniques.

BRIEF DESCRIPTION OF THE INVENTION

In accordance with the principles of this invention, a unique universal tray and sample holder system permits a wide variety of samples to be accurately positioned at the focal plane of a solid state, slow scan camera and illuminated appropriately for the labeling technique employed. Thus, the tray and sample holder system permits the implementation of a multi-mode imaging apparatus for the various labeling techniques and sample types.

The tray, illustratively, is a simple rectangular-shaped container with a transparent (to U V and visible light) base and upstanding side walls. The camera is pre-focused to establish a focal plane near the top of the side walls. The side walls are adapted to receive a sample holder in a position to properly place a sample at the focal plane by placing the sample at different elevations with respect to the side walls depending on the labeling mode employed and the type of sample to be imaged. In some instances, the sample is sandwiched in a multi-layered sample holder which is inserted into the tray. The tray includes means to fix the elevation of the sample holder keyed to the labeling mode employed. Thus, focusing the image becomes a simple problem of using the sample holder which corresponds to the selected labeling mode. The proper elevation of the sample to the focal plane and the proper alignment in the field of the camera is automatically achieved regardless of the labeling mode employed. Also, transparent, translucent, or opaque base plates and/or cover plates may be used depending on the illumination required for the selected illumination mode.

In one embodiment, the tray is adapted to accept a slab gel sample directly for imaging using fluorescence. In another, the sample holder is adapted to accept a blot membrane sandwiched between a base and a transparent cover so that the membrane is properly positioned at the pre-established focal plane for fluorescent illumination. In another, the sample holder is adapted to accept a blot membrane in a sealed bag sandwiched between a phosphor screen and an opaque plate to properly position the phosphor screen at the focal plane for radioisotope detection. in each instance, the sample and sample holder, in which it is contained, is of a thickness such that when it is installed in the sample holder in the tray, the sample is correctly positioned at the focal plane.

Sample holders also are provided for other types of samples such as storage phosphor plates, micro titer plates and films. Specifically, the sample holders are adapted to accept a storage phosphor plate for the proper focal plane positioning for storage phosphor plate read out, a micro plate holder for micro titer plate imaging, and a film sandwiched between a transparent cover and a translucent base for densitometry measurement.

The ability of the tray and sample holder system to position a sample always at the focal plane of the imaging system and with correct alignment also permits the inclusion of multiple illumination sources in a single apparatus for implementing all techniques for sample illumination, labeling mode, and image capture from any radiation emitting or absorbing sample.

The unique tray and sample holder system permits the use of flood light illumination rather than the conventional practice of sequentially scanning by laser for parallel read out of a latent image stored on a storage phosphor plate.

DETAILED DESCRIPTION OF ILLUSTRATIVE EMBODIMENTS

Figure 1:
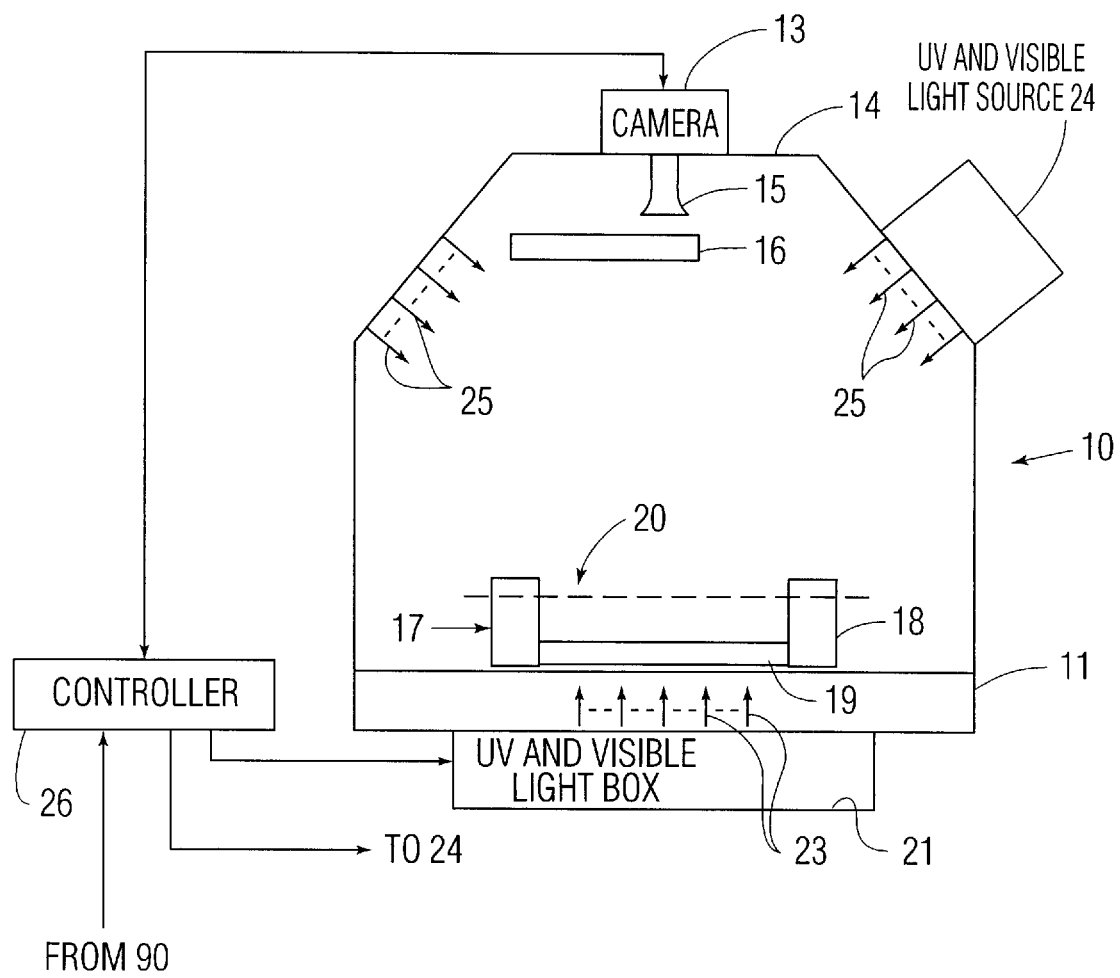
FIG. 1 is a schematic illustration of a multi-mode apparatus in accordance with the principles of this invention.

FIG. 1 shows a multi-mode apparatus for sensing light patterns from a radiation emitting or absorbing sample. The apparatus includes a housing 11 with a solid state camera 13 positioned at it's top surface 14. The camera is a solid state, digital camera, preferably a cooled, scientific CCD camera. The camera is aimed downward, as viewed in the figure, through a lens 15 and a filter wheel 16.

A tray 17 is positioned at the bottom of apparatus 10. The tray has upstanding walls 18 and is adapted to receive different sample-positioning sample holders to always position a sample at a pre-specified focal plane represented by broken line 20.

The apparatus also includes a plurality of light sources differently positioned for providing illumination for different labeling modes. The first of these illumination sources is light box 21 for flood lighting (trans illuminating) a sample, with either visible or ultra violet (UV) light as indicated by vertical arrows 23. The second of these illumination sources is a source 24 consisting UV and visible light sources of different specific wavelengths (i. e. 600 nm, 514 nm, and 450 nm) for different epi sample illumination techniques. The radiation from source 24 is directed downward at tray 17 as indicated by arrows 25. Operation of the apparatus is under the control of controller 26 which may be a computer.

Controller 26 can selectively activate individual sources within 24 to select specific UV or visible wavelengths for illumination. Similarly, controller 26 can select either UV or visible trans illumination in source 21. Controller 26 can also select any particular filter in filter wheel 16. By selecting appropriate illumination wavelengths with sources 24 or 21 and by selecting a filter within filter wheel 16, the controller can allow multi-mode imaging to match the sample in tray 18.

Figure 2:
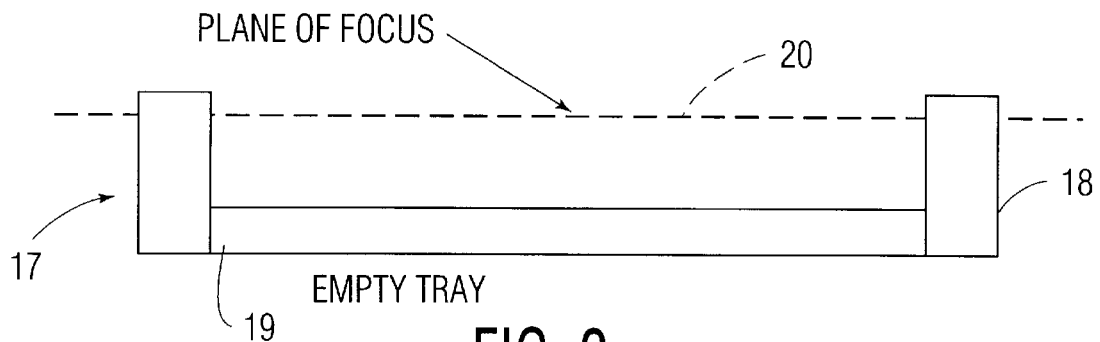
FIGS. 2 through 8 are schematic illustrations of a tray and sample holder system for proper focal plane positioning of samples for the apparatus of FIG. 1.

FIG. 2 shows the tray 17 of FIG. 1 with upstanding side walls 18 with a plane of focus 20 defined as indicated. The tray is adapted to accept sample holders which hold the sample which typically emits the light pattern to be captured by camera 13. Depending on the selected labeling mode, the sample holder has a different thickness and optical transmission characteristics and, thus, has to be positioned at a different elevation with respect to the side walls in order for the sample to be at the focal plane.

Figure 3:
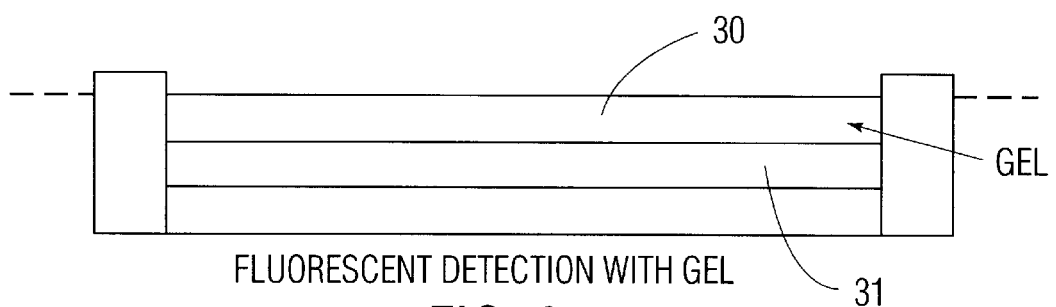

FIGS. 3 through 8 illustrate the positions of sample holders in tray 17 for different labeling modes. FIG. 3, specifically, provides for positioning a gel 30 with it's emission plane aligned with the plane of focus as shown in the figure. The sample is positioned for epi-illumination from source 24 to generate a fluorescent pattern for capture by camera 13 under the control of controller 26; the use of UV illumination from source 21 together with the translucent (UV translucent) base plate 31, on the other hand, provides for trans illumination. An appropriate filter is selected in filter wheel 16 so as to reject the illumination wavelength but to allow the camera to see the fluorescent image at it's different wavelength.

Figure 4:
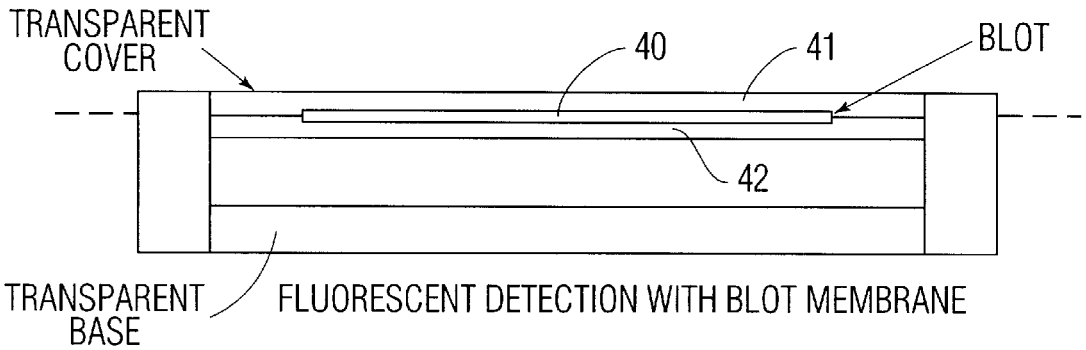

FIG. 4 illustrates a sample holder for positioning a blot membrane 40 in tray 17. The blot membrane is sandwiched between a transparent cover 41 and a transparent base 42 and, again, is epi-illuminated by source 24 and filtered by filter wheel 16 to generate a fluorescent image. Chemiluminescent-labeled blots can be imaged by turning off all illumination sources and by performing a longer time exposure with camera 13.

Figure 5:
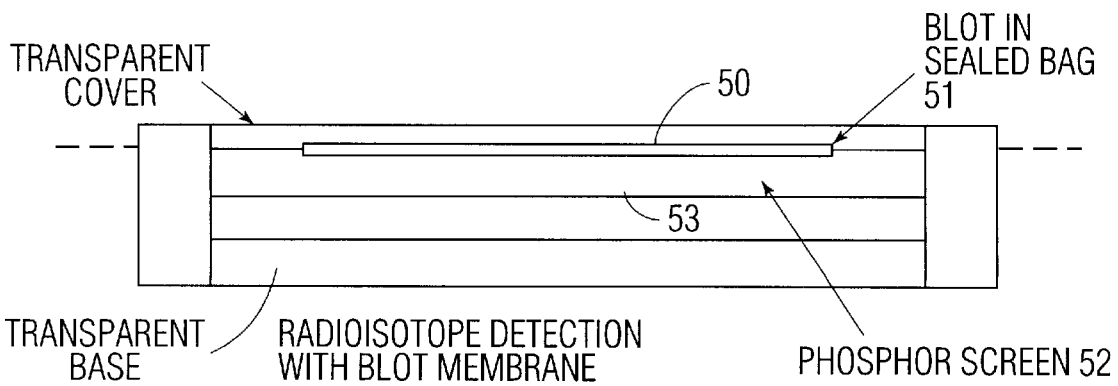

FIG. 5 illustrates a sample holder for positioning a blot membrane, radioisotope-labeled and enclosed in a sealed bag 51. The sealed bag is sandwiched between a phosphor intensifier screen 52 and an opaque plate 53. The phosphor screen converts radioisotope emission from the blot membrane into visible light which is captured by camera 13 with a time exposure.

Phosphor intensifier screens are designed for use with film and have emission wavelengths in the blue or green regions of the spectrum. CCD cameras are more sensitive to red light. Readily available fluorescent reagents which absorb in the blue and emit in the red are useful in conjunction with blue-emitting phosphor screens to convert photons to the red portion of the spectrum, to increase instrument sensitivity.

Figure 6:
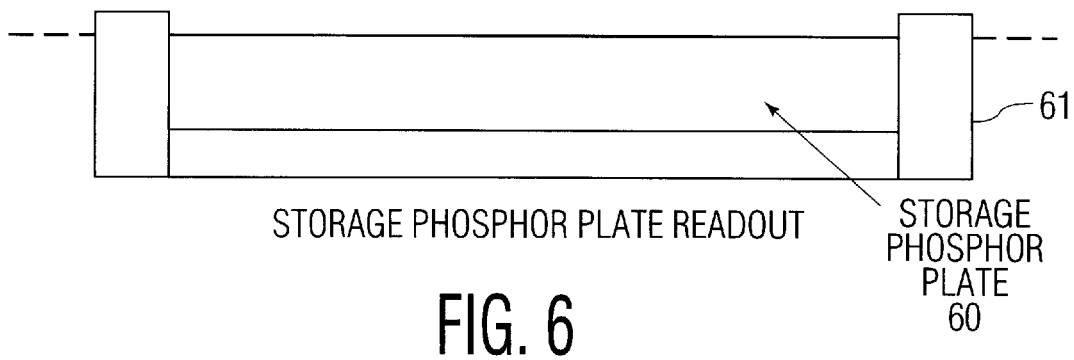

FIG. 6 illustrates the use of a storage phosphor plate 60 positioned on sample holder 61 for image capture. To capture the latent image on the storage phosphor plate, 600 nm red light is selected in source 24 to flood the plate. All emissions from the storage phosphor are then recorded simultaneously with camera 13 using a filter in filter wheel 16 that blocks the 600 nm excitation light.

Figure 7:
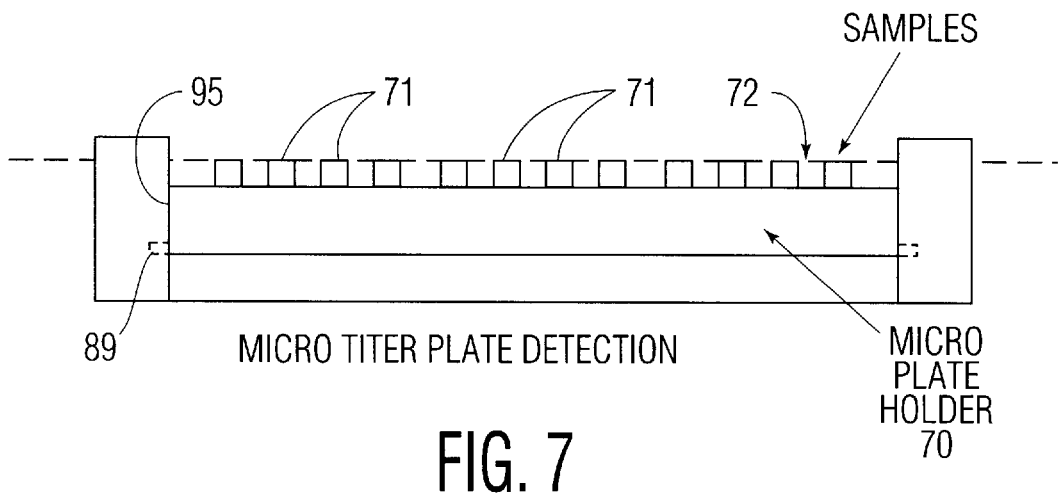

FIG. 7 illustrates the use of a sample holder which accepts a micro titer plate holder 70 for samples 71, positioning the top of the samples at focal plane 72 for either fluorescent micro titer plate imaging using source 24 or source 21 or chemiluminescent imaging with all illumination sources turned off.

Figure 8:
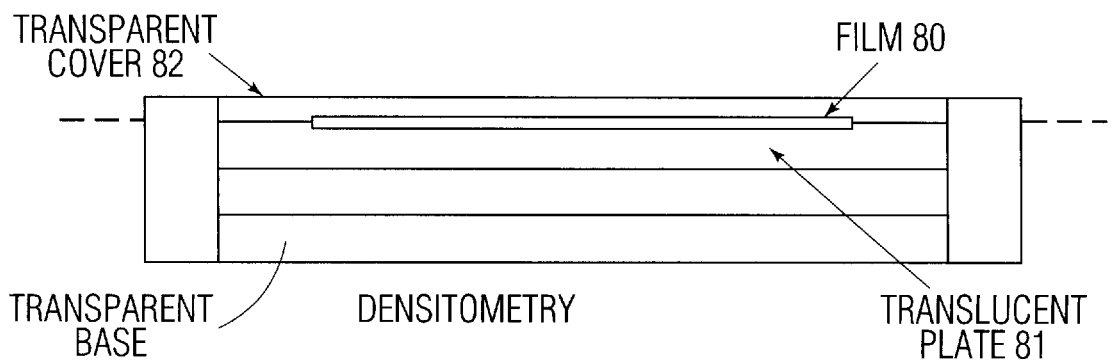

FIG. 8 illustrates a sample holder for densitometry imaging of a photographic film. The sample holder comprises a film 80 sandwiched between a translucent plate 81 and a transparent cover 82. A visible source illumination 21 is used to illuminate the film. The translucent plate 81 disperses the light from source 21 to form a relatively uniform source. To calibrate the densitometry, the camera 13 can be used first to capture an image of the sample holder without a film sample. This will result in an image of the illumination pattern in translucent plate 81. The image of the film sample then can be "flat field" corrected using the image of the translucent plate.

A comparison of the illustrations in FIGS. 3 through 8 indicates that the sample holder positions vary and thus have to be located at different elevations with respect to the side walls of the tray in order to position the samples at the pre-focused focal plane. The positioning can be accomplished in a variety of simple ways. One convenient positioning technique is to have the side walls of the tray grooved to different depths. By having sample holders with corresponding extensions for each different groove pattern, sample holders can be positioned easily. An illustrative extension arrangement is designated 89 in FIG. 7. An optical sensor may be positioned at the bottom of each groove to signal the controller to activate the proper illuminator and to establish the timing, the appropriate filter, exposure . . . etc. for the mode selected. Such a sensor is identified by the numeral 90 in FIG. 9.

Figure 9:
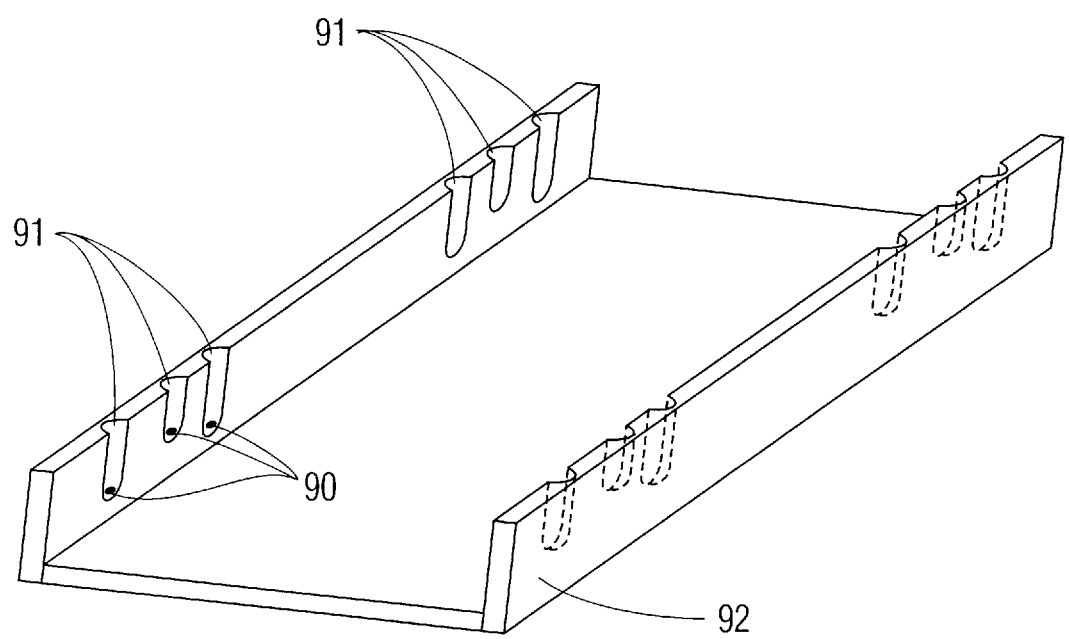
FIG. 9 is a schematic perspective view of a tray positioning arrangement for the sample holders shown in FIGS. 3 through 8.

FIG. 9 illustrates such a positioning arrangement where grooves 91 extend downward (as viewed) from the top of a tray 92. The grooves are of different depths to correspond to extensions 89 extending from the inner face 95 of a sample holder 70 in FIG. 7.

The use of sample holders of the type shown in FIGS. 2 through 8 with, for example, the grooved tray of FIG. 9 permits the proper placement of a sample at the pre-focused focal plane of the apparatus of FIG. 1. It also permits the sample to be aligned correctly to the field of view of the camera 13, by fixing the position of tray 18 within the apparatus of FIG. 1. In the absence of such a tray and sample holder system, there is no easy way to observe an image in real time for pre-focusing and aligning a sample due to the fact that the camera (13) employed for such image capture, is a "slow scan" read out camera as mentioned hereinbefore. A tray and sample holder system as described herein always positions a sample correctly for different sample types regardless of the illumination mode employed. The use of the unique tray and sample holder system of FIGS. 2 through 9 permits the implementation of the multi-mode apparatus of FIG. 1 wherein a plurality of different light sources can be provided in a single apparatus, the particular combination of light source, sample holder, and filter wheel being under the control of a user operating the controller of FIG. 1.

The initial setting of the focal plane in FIG. 2 through 8 is carried out by placing a resolution target in a sample holder and by operating the camera in a mode in which small sub arrays of the CCD camera are read out to produce a frame rate of several frames per second which is adequate for focusing onto a target of this type. An image is then captured at full resolution to ensure that optimal focus has been achieved. The camera optics then are sealed in position and the pre-focused focal plane of FIGS. 2 through 8 is set.

What is claimed is:

1. Multi-mode apparatus for capturing a light image from a planar sample, said apparatus comprising a solid state camera defining a focal plane in said apparatus, said apparatus including a tray, said apparatus including means for positioning said tray in the field of view of said camera, said tray including means for accepting sample holders at different elevations, each of said sample holders being of a configuration for accepting an associated sample, said means for accepting including means for positioning said sample holder at a different elevation in said tray for positioning said sample at said focal plane.

2. Apparatus as in claim 1 wherein said camera is a CCD camera.

3. Apparatus as in claim 2 wherein said CCD camera is a cooled CCD camera operated in the slow scan mode.

4. Apparatus as set forth in claim 3 wherein said planar sample comprises an electropheresis gel wherein said sample holder includes means for positioning said gel such that the top surface thereof is in said focal plane.

5. Apparatus as in claim 3 wherein said planar sample comprises a blot membrane and said sample holder comprises said membrane sandwiched between a transparent cover and a translucent base plate.

6. Apparatus as in claim 3 wherein said planar sample comprises a blot membrane in a sealed bag and said sample holder comprises said sealed bag sandwiched between a transparent cover and a phosphor screen.

7. Apparatus as in claim 3 wherein said sample holder comprises a micro titer plate holder having a plurality of samples arranged on the top surface thereof at said focal plane.

8. Apparatus as in claim 3 wherein said sample holder comprises a storage phosphor plate which has a stored light pattern therewithin.

9. Apparatus as in claim 3 wherein said planar sample comprises a film and said sample holder comprises said film sandwiched between a transparent cover and a translucent plate.

10. Apparatus as in claim 1 wherein said planar sample comprises an electropheresis gel and said sample holder includes means for positioning said gel such that the top surface thereof is coplanar with said focal plane.

11. Apparatus as in claim 1 wherein said planar sample comprises a blot membrane and said sample holder comprises said membrane sandwiched between a transparant cover and a translucent base plate.

12. Apparatus as in claim 1 wherein said planar sample comprises a blot membrane in a sealed bag and said sample holder comprises said sealed bag sandwiched between a plate and a phosphor screen.

13. Apparatus as in claim 1 wherein said sample holder comprises a storage phosphor plate which has a stored light pattern therewithin.

14. Apparatus as in claim 1 wherein said sample holder comprises a micro titer plate holder having a plurality of samples arranged on the top surface thereof at said focal plane.

15. Apparatus as in claim 1 wherein said planar sample comprises a film and said sample holder comprises said film sandwiched between a transparent cover and a translucent plate.

16. Apparatus for capturing a light image from a planar sample positioned in a focal plane, said apparatus including a tray and sample holder system, said system comprising a set of sample holders of different configurations, each of said sample holders having a unique configuration to accept a sample in a corresponding specified labeling mode, each of said sample holders including means communicating with said tray for properly positioning said sample holder for positioning a sample therewithin in said focal plane.

17. Apparatus as in claim 16 also including a cooled, slow scan CCD camera positioned therein for defining said focal plane.

18. Apparatus as in claim 16 wherein said tray includes side walls, each of said side walls including uniquely-placed sets of slots of differing depths, said means communicating including means extending differently from each of said sample holders to engage only a corresponding one of said sets of slots for properly positioning the sample holder.

19. A tray and sample holder system, said system comprising a set of sample holders of different configurations, each of said sample holders having a unique configuration to accept a sample in a corresponding labeling mode, each of said said sample holders including means for communicating with said tray for properly positioning said sample holders for positioning a sample therewithin in a preset plane.

* * * * *